(12) United States Patent
Lamson et al.

(10) Patent No.: US 9,149,266 B2
(45) Date of Patent: Oct. 6, 2015

(54) DEFORMING ANCHOR DEVICE

(75) Inventors: Theodore C. Lamson, Pleasanton, CA (US); Joseph Catanese, III, San Leandro, CA (US); Floria Cheng, San Francisco, CA (US); Matthew McLean, San Francisco, CA (US)

(73) Assignee: NeoTract, Inc., Pleasanton, CA (US)

(*) Notice: Subject to any disclaimer, the term of this patent is extended or adjusted under 35 U.S.C. 154(b) by 539 days.

(21) Appl. No.: 12/852,748

(22) Filed: Aug. 9, 2010

(65) Prior Publication Data

US 2011/0040312 A1 Feb. 17, 2011

Related U.S. Application Data

(63) Continuation-in-part of application No. 12/852,243, filed on Aug. 6, 2010, now Pat. No. 8,333,776, which is a continuation-in-part of application No. 12/512,674, filed on Jul. 30, 2009, now Pat. No. 8,216,254, said application No. 12/852,748 is a continuation-in-part of application No. 11/775,162, filed on Jul. 9, 2007, now Pat. No. 8,945,152, and a continuation-in-part of (Continued)

(51) Int. Cl.
| A61B 17/10 | (2006.01) |
| A61B 17/04 | (2006.01) |
| A61B 17/02 | (2006.01) |
| A61B 17/00 | (2006.01) |

(52) U.S. Cl.
CPC .......... *A61B 17/0401* (2013.01); *A61B 17/0218* (2013.01); *A61B 2017/00867* (2013.01); *A61B 2017/042* (2013.01); *A61B 2017/0417* (2013.01); *A61B 2017/0446* (2013.01); *A61B 2017/0454* (2013.01)

(58) Field of Classification Search
USPC .......................................................... 606/232
See application file for complete search history.

(56) References Cited

U.S. PATENT DOCUMENTS

| 659,422 | A | 10/1900 | Shidler |
| 780,392 | A | 1/1905 | Wanamaker et al. |
| 789,467 | A | 5/1905 | West |
| 2,579,192 | A | 12/1951 | Kohl |
| 2,646,298 | A | 7/1953 | Leary |
| 2,697,624 | A | 12/1954 | Thomas |
| 2,734,299 | A | 2/1956 | Masson |
| 2,825,592 | A | 3/1958 | Semple |
| 3,326,586 | A | 6/1967 | Frost et al. |
| 3,470,834 | A | 10/1969 | Bone |
| 3,521,918 | A | 7/1970 | Hammond |
| 3,713,680 | A | 1/1973 | Pagano |
| 3,716,058 | A | 2/1973 | Tanner, Jr. |
| 3,756,638 | A | 9/1973 | Stockberger |

(Continued)

FOREIGN PATENT DOCUMENTS

| DE | 10159470 | 6/2003 |
| EP | 0246836 | 12/1991 |

(Continued)

OTHER PUBLICATIONS

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

(Continued)

*Primary Examiner* — Gregory Anderson

(57) ABSTRACT

An anchor that secures to a connector as part of an anchor assembly is disclosed. The proximal anchor includes deformable structure for engaging a connector.

16 Claims, 13 Drawing Sheets

Related U.S. Application Data application No. 11/671,914, filed on Feb. 6, 2007, now Pat. No. 8,157,815, and a continuation-in-part of application No. 11/492,690, filed on Jul. 24, 2006, now Pat. No. 7,896,891, and a continuation-in-part of application No. 11/833,660, filed on Aug. 3, 2007, now Pat. No. 8,940,001, which is a continuation of application No. 11/318,246, filed on Dec. 22, 2005, now Pat. No. 7,645,286, said application No. 12/852,748 is a continuation-in-part of application No. 11/838,036, filed on Aug. 13, 2007, now Pat. No. 7,914,542, which is a continuation of application No. 11/134,870, filed on May 20, 2005, now Pat. No. 7,758,594.

(60) Provisional application No. 61/084,937, filed on Jul. 30, 2008.

(56) References Cited

U.S. PATENT DOCUMENTS

| | | |
|---|---|---|
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,078,731 A * | 1/1992 | Hayhurst .................. 606/232 |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,269,809 A | 12/1993 | Hayhurst et al. |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | De la Torre |
| 5,480,406 A | 1/1996 | Nolan et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,649 A | 11/1997 | Li |
| 5,690,677 A | 11/1997 | Schmiedling et al. |
| 5,697,950 A | 12/1997 | Fucci et al. |
| 5,707,394 A | 1/1998 | Miller et al. |
| 5,716,368 A | 2/1998 | De la Torre |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyer et al. |
| 5,810,848 A | 9/1998 | Hayhurst |
| 5,814,072 A | 9/1998 | Bonutti |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,897,574 A | 4/1999 | Bonutti |
| 5,899,911 A | 5/1999 | Carter |
| 5,899,921 A | 5/1999 | Caspari et al. |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Wilard |
| 5,971,447 A | 10/1999 | Steck, III |
| 6,010,514 A | 1/2000 | Burney et al. |
| 6,011,525 A | 1/2000 | Piole |
| 6,015,428 A * | 1/2000 | Pagedas .................. 606/232 |
| 6,030,393 A | 2/2000 | Corlew |

(56) References Cited

U.S. PATENT DOCUMENTS

| | | | |
|---|---|---|---|
| 6,033,430 A | 3/2000 | Bonutti | |
| 6,036,701 A | 3/2000 | Rosenman | |
| 6,048,351 A | 4/2000 | Gordon et al. | |
| 6,053,908 A | 4/2000 | Crainich et al. | |
| 6,056,722 A | 5/2000 | Jayaraman | |
| 6,056,772 A | 5/2000 | Bonutti | |
| 6,068,648 A | 5/2000 | Cole et al. | |
| 6,080,167 A | 6/2000 | Lyell | |
| 6,086,608 A | 7/2000 | Ek et al. | |
| 6,110,183 A | 8/2000 | Cope | |
| 6,117,160 A | 9/2000 | Bonutti | |
| 6,117,161 A | 9/2000 | Li et al. | |
| 6,120,539 A | 9/2000 | Eldridge et al. | |
| 6,139,555 A | 10/2000 | Hart et al. | |
| RE36,974 E | 11/2000 | Bonutti | |
| 6,143,006 A | 11/2000 | Chan | |
| 6,159,234 A | 12/2000 | Bonutti et al. | |
| 6,200,329 B1 | 3/2001 | Fung et al. | |
| 6,206,895 B1 | 3/2001 | Levinson | |
| 6,228,096 B1 | 5/2001 | Marchand | |
| 6,258,124 B1 | 7/2001 | Darois et al. | |
| 6,261,302 B1 | 7/2001 | Voegele et al. | |
| 6,270,530 B1 | 8/2001 | Eldridge et al. | |
| 6,280,460 B1 | 8/2001 | Bolduc et al. | |
| 6,290,711 B1 | 9/2001 | Caspari et al. | |
| 6,312,448 B1 | 11/2001 | Bonutti | |
| 6,319,263 B1 | 11/2001 | Levinson | |
| 6,322,112 B1 | 11/2001 | Duncan | |
| 6,332,889 B1 | 12/2001 | Sancoff et al. | |
| 6,398,795 B1 | 6/2002 | McAllister et al. | |
| 6,425,900 B1 | 7/2002 | Knodel et al. | |
| 6,428,562 B2 | 8/2002 | Bonutti | |
| 6,436,107 B1 | 8/2002 | Wang et al. | |
| 6,461,355 B2 | 10/2002 | Svejkovsky et al. | |
| 6,482,235 B1 | 11/2002 | Lambrecht et al. | |
| 6,488,691 B1 | 12/2002 | Carroll et al. | |
| 6,491,707 B2 | 12/2002 | Makower et al. | |
| 6,494,888 B1 | 12/2002 | Laufer et al. | |
| 6,500,195 B2 | 12/2002 | Bonutti | |
| 6,506,190 B1 | 1/2003 | Walshe | |
| 6,506,196 B1 | 1/2003 | Laufer | |
| 6,517,569 B2 | 2/2003 | Mikus et al. | |
| 6,527,702 B2 | 3/2003 | Whalen et al. | |
| 6,527,794 B1 | 3/2003 | McDevitt et al. | |
| 6,530,932 B1 | 3/2003 | Swayze et al. | |
| 6,533,796 B1 | 3/2003 | Sauer et al. | |
| 6,547,725 B1 | 4/2003 | Paolitto et al. | |
| 6,551,328 B2 | 4/2003 | Kortenbach | |
| 6,551,333 B2 | 4/2003 | Kuhns et al. | |
| 6,565,578 B1 | 5/2003 | Peifer et al. | |
| 6,569,187 B1 | 5/2003 | Bonutti et al. | |
| 6,572,626 B1 | 6/2003 | Knodel et al. | |
| 6,572,635 B1 | 6/2003 | Bonutti | |
| 6,572,653 B1 | 6/2003 | Simonson | |
| 6,582,453 B1 * | 6/2003 | Tran et al. | 606/232 |
| 6,592,609 B1 | 7/2003 | Bonutti | |
| 6,596,013 B2 | 7/2003 | Yang et al. | |
| 6,599,311 B1 | 7/2003 | Biggs et al. | |
| 6,626,913 B1 | 9/2003 | McKinnon et al. | |
| 6,626,916 B1 | 9/2003 | Yeung et al. | |
| 6,626,919 B1 | 9/2003 | Swanstrom | |
| 6,629,534 B1 | 10/2003 | St. Goar et al. | |
| 6,641,592 B1 | 11/2003 | Sauer et al. | |
| 6,656,182 B1 | 12/2003 | Hayhurst | |
| 6,660,008 B1 * | 12/2003 | Foerster et al. | 606/327 |
| 6,660,023 B2 | 12/2003 | McDevitt et al. | |
| 6,663,589 B1 | 12/2003 | Halevy | |
| 6,663,639 B1 | 12/2003 | Laufer et al. | |
| 6,699,263 B2 | 3/2004 | Cope | |
| 6,706,047 B2 | 3/2004 | Trout et al. | |
| 6,709,493 B2 | 3/2004 | DeGuiseppi et al. | |
| 6,715,804 B2 | 4/2004 | Beers | |
| 6,719,709 B2 | 4/2004 | Whalen et al. | |
| 6,730,112 B2 | 5/2004 | Levinson | |
| 6,736,823 B2 | 5/2004 | Darois et al. | |
| 6,736,854 B2 | 5/2004 | Vadurro et al. | |
| 6,740,098 B2 | 5/2004 | Abrams et al. | |
| 6,767,037 B2 | 7/2004 | Wenstrom, Jr. | |
| 6,770,076 B2 | 8/2004 | Foerster | |
| 6,773,438 B1 | 8/2004 | Knodel et al. | |
| 6,773,441 B1 | 8/2004 | Laufer et al. | |
| 6,790,213 B2 | 9/2004 | Cherok et al. | |
| 6,802,846 B2 | 10/2004 | Hauschild et al. | |
| 6,821,282 B2 | 11/2004 | Perry et al. | |
| 6,821,285 B2 | 11/2004 | Laufer et al. | |
| 6,821,291 B2 | 11/2004 | Boleg et al. | |
| 6,835,200 B2 | 12/2004 | Laufer et al. | |
| 6,905,475 B2 | 6/2005 | Hauschild et al. | |
| 6,908,473 B2 | 6/2005 | Skiba et al. | |
| 6,926,732 B2 | 8/2005 | Derus et al. | |
| 6,951,565 B2 | 10/2005 | Keane et al. | |
| 6,986,775 B2 | 1/2006 | Morales et al. | |
| 6,991,596 B2 | 1/2006 | Whalen et al. | |
| 6,991,647 B2 | 1/2006 | Jadhav | |
| 6,997,940 B2 | 2/2006 | Bonutti | |
| 7,001,327 B2 | 2/2006 | Whalen et al. | |
| 7,011,688 B2 | 3/2006 | Gryska et al. | |
| 7,015,253 B2 | 3/2006 | Escandon et al. | |
| 7,048,698 B2 | 5/2006 | Whalen et al. | |
| 7,048,747 B2 | 5/2006 | Arcia et al. | |
| 7,060,077 B2 | 6/2006 | Gordon et al. | |
| 7,081,126 B2 | 7/2006 | McDevitt et al. | |
| 7,083,638 B2 | 8/2006 | Foerster | |
| 7,087,073 B2 | 8/2006 | Bonutti | |
| 7,089,064 B2 | 8/2006 | Manker et al. | |
| 7,090,690 B2 | 8/2006 | Foerster et al. | |
| 7,093,601 B2 | 8/2006 | Manker et al. | |
| 7,105,004 B2 | 9/2006 | Dicesare et al. | |
| 7,108,655 B2 | 9/2006 | Whalen et al. | |
| 7,141,038 B2 | 11/2006 | Whalen et al. | |
| 7,153,314 B2 | 12/2006 | Laufer et al. | |
| 7,179,225 B2 | 2/2007 | Shluzas | |
| 7,226,558 B2 | 6/2007 | Nieman et al. | |
| 7,232,448 B2 | 6/2007 | Battles et al. | |
| 7,288,063 B2 | 10/2007 | Petros et al. | |
| 7,303,108 B2 | 12/2007 | Shelton, IV | |
| 7,320,701 B2 | 1/2008 | Haut et al. | |
| 7,322,974 B2 | 1/2008 | Swoyer et al. | |
| 7,334,822 B1 | 2/2008 | Hines et al. | |
| 7,340,300 B2 | 3/2008 | Christopherson et al. | |
| 7,399,304 B2 | 7/2008 | Gambale et al. | |
| 7,402,166 B2 | 7/2008 | Feigl | |
| 7,416,554 B2 | 8/2008 | Lam et al. | |
| 7,553,317 B2 | 6/2009 | Wesenburgh, II et al. | |
| 7,608,108 B2 | 10/2009 | Bhatnager et al. | |
| 7,658,311 B2 | 2/2010 | Boudreaux | |
| 7,674,275 B2 | 3/2010 | Martin et al. | |
| 7,695,494 B2 * | 4/2010 | Foerster | 606/232 |
| 7,727,248 B2 | 6/2010 | Smith et al. | |
| 2001/0044639 A1 | 11/2001 | Levinson | |
| 2002/0095154 A1 | 7/2002 | Atkinson et al. | |
| 2002/0128684 A1 | 9/2002 | Foerster | |
| 2002/0161382 A1 | 10/2002 | Neisz et al. | |
| 2002/0193809 A1 | 12/2002 | Meade | |
| 2003/0109769 A1 | 6/2003 | Lowery et al. | |
| 2003/0191497 A1 | 10/2003 | Cope | |
| 2003/0204195 A1 | 10/2003 | Keane et al. | |
| 2004/0030217 A1 | 2/2004 | Yeung et al. | |
| 2004/0043052 A1 | 3/2004 | Hunter et al. | |
| 2004/0078046 A1 | 4/2004 | Barzell et al. | |
| 2004/0193191 A1 | 9/2004 | Starksen et al. | |
| 2004/0193194 A1 | 9/2004 | Laufer et al. | |
| 2004/0194790 A1 | 10/2004 | Laufer et al. | |
| 2004/0243178 A1 | 12/2004 | Haut et al. | |
| 2004/0243179 A1 | 12/2004 | Foerster | |
| 2004/0243180 A1 | 12/2004 | Donnelly | |
| 2004/0243227 A1 | 12/2004 | Starksen et al. | |
| 2004/0260345 A1 | 12/2004 | Foerster | |
| 2005/0055087 A1 | 3/2005 | Starksen | |
| 2005/0065550 A1 | 3/2005 | Starksen et al. | |
| 2005/0107811 A1 | 5/2005 | Starksen et al. | |
| 2005/0107812 A1 | 5/2005 | Starksen et al. | |
| 2005/0154401 A1 | 7/2005 | Weldon et al. | |
| 2005/0177181 A1 | 8/2005 | Kagen et al. | |

(56) References Cited

U.S. PATENT DOCUMENTS

| | | |
|---|---|---|
| 2005/0203344 A1 | 9/2005 | Orban, III et al. |
| 2005/0203550 A1 | 9/2005 | Laufer et al. |
| 2005/0216078 A1 | 9/2005 | Starksen et al. |
| 2005/0267405 A1 | 12/2005 | Shah |
| 2005/0273138 A1 | 12/2005 | Starksen et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0265042 A1 | 11/2006 | Catanese, III et al. |
| 2006/0282081 A1 | 12/2006 | Fanton et al. |
| 2007/0049929 A1 | 3/2007 | Catanese, III |
| 2007/0049970 A1 | 3/2007 | Belef et al. |
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2009/0012537 A1 | 1/2009 | Green |
| 2010/0010631 A1 | 1/2010 | Otte et al. |
| 2010/0063542 A1* | 3/2010 | van der Burg et al. ........ 606/232 |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Accepted Jun. 7, 2006.

Richard Berges et al., "Alternative Minimalinvasive Therapien Beim Benignen Prostatasyndrom", medizin, Jg, 104 heft 37, Sep. 14, 2007.

Rudolf Hartung, et al., Instrumentelle Therapie der benegnen Prostatahyperplasie, Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 194(36):A2424-9.

R. Hubmann, Geschichte der transurethralen Prostataeingriffe, Geschichte der Medizin, Urologe [B] 2000 40:152-160.

U. Jonas, et al. Benigne Prostatahyperplasie, Der Urologe 2006, [Sonderheft] 45: 134-144.

O.A. Bacharova, et al. "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 209; 16 (1):19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8 No. 8, p. 35-39.

O. Reich, et al., "Benignes Prostatasyndrom (BPS)", er Urologe A Issue vol. 45, No. 6, Jun. 2006, p. 769-782.

Daito Takashi, "Low-Invasive Treatment for BPH", Medico vol. 34, No. 10 p. 366-369.

Trapeznikov et al., "New Technologies in the Treatment of Benign Prostatic Hyperplasia", Urologia Nefrol (Mosk), Jul.-Aug. 1996 (4): 41-47.

Koyanagi Tomohiko, et al., "Surgery View of 21st Century", Urological Surgery, vol. 84, No. 1 p. 47-53.

Borzhievski et al., "Tactics of the Surgical Treatment of Patients With Prostatic Adenoma and Acute Urinary Retention", Urologia Nefrol (Mosk)., Jan.-Feb. 1987 (1): 39-43.

Yeung, Jeff, "Treating Urinary Stress Incontinence Without Incision with Endoscopic Suture Anchor & Approximating Device," Aleeva Medical, Inc., 2007.

* cited by examiner

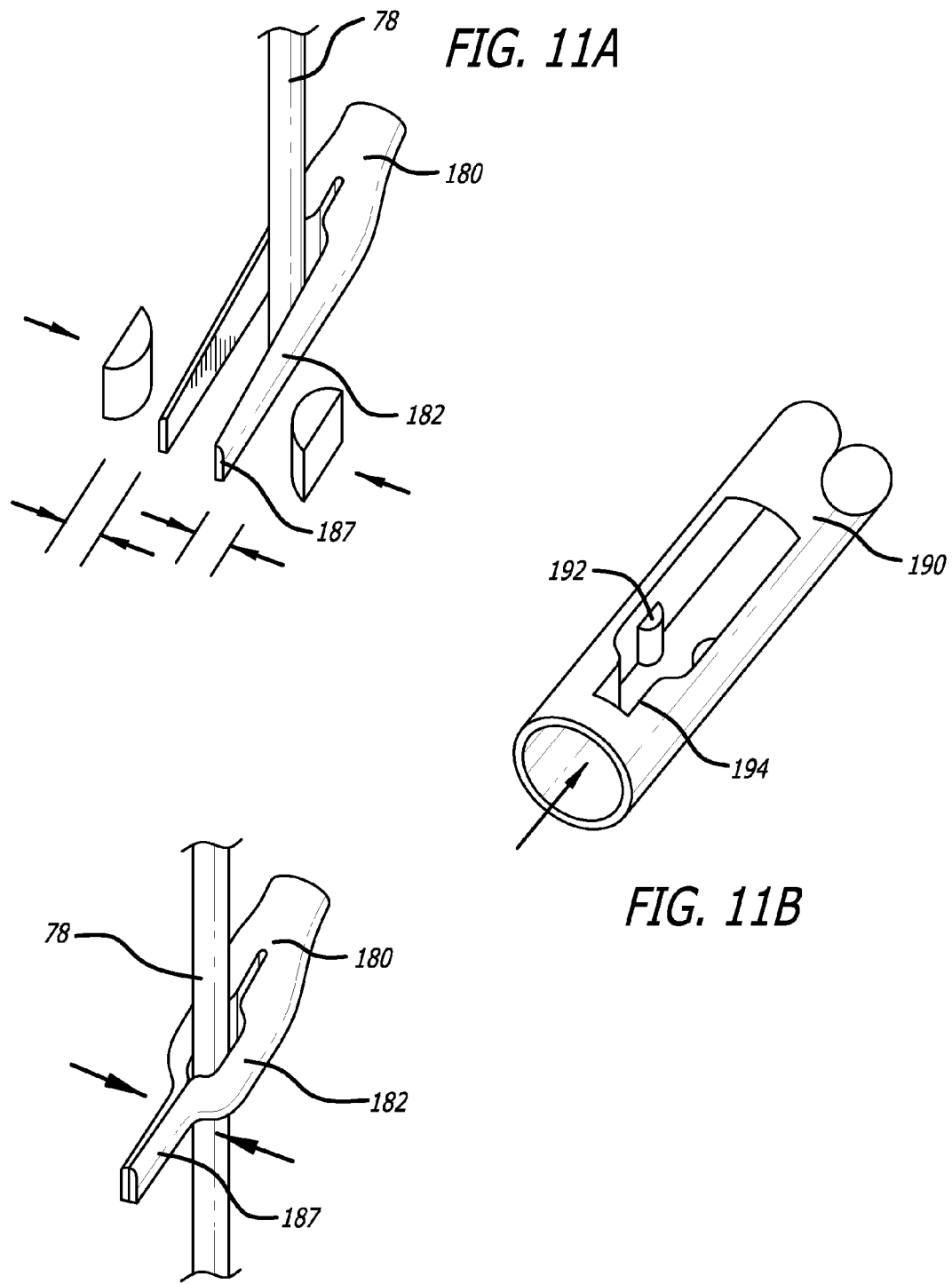

DEFORMING ANCHOR DEVICE

This application is a continuation-in-part of: 1) U.S. patent application Ser. No. 12/852,243, filed Aug. 6, 2010; 2) U.S. patent application Ser. No. 12/512,674, filed Jul. 30, 2009 which claims the benefit of Provisional Application Ser. No. 61/084,937; 3) U.S. patent application Ser. No. 11/775,162, filed Jul. 9, 2007; 4) U.S. patent application Ser. No. 11/671,914, filed Feb. 6, 2007; 5) U.S. patent application Ser. No. 11/492,690, filed on Jul. 24, 2006; 6) U.S. patent application Ser. No. 11/833,660, filed on Aug. 3, 2007, which is a continuation of U.S. patent application Ser. No. 11/318,246, filed on Dec. 20, 2005; and 7) U.S. patent application Ser. No. 11/838,036 filed on Aug. 13, 2007, which is a continuation of U.S. patent application Ser. No. 11/134,870 filed on May 20, 2005; the entire disclosures of each of which are expressly incorporated herein by reference.

FIELD OF THE INVENTION

The disclosed embodiments relate generally to medical devices and methods, and more particularly to systems and associated methods for manipulating or retracting tissues and anatomical or other structures within the body of human or animal subjects for the purpose of treating diseases or disorders.

BACKGROUND

There are a wide variety of situations in which it is desirable to lift, compress or otherwise reposition normal or aberrant tissues or anatomical structures (e.g., glands, organs, ligaments, tendons, muscles, tumors, cysts, fat pads, and the like) within the body of a human or animal subject. Such procedures are often carried out for the purpose of treating or palliating the effects of diseases or disorders (e.g., hyperplasic conditions, hypertrophic conditions, neoplasias, prolapses, herniations, stenoses, constrictions, compressions, transpositions, congenital malformations, and the like) and/or for cosmetic purposes (e.g., face lifts, breast lifts, brow lifts, and the like) and/or for research and development purposes (e.g., to create animal models that mimic various pathological conditions). In many of these procedures, surgical incisions are made in the body, and laborious surgical dissection is performed to access and expose the affected tissues or anatomical structures. Thereafter, in some cases, the affected tissues or anatomical structures are removed or excised. In other cases, various natural or man-made materials are used to lift, sling, reposition or compress the affected tissues.

Benign Prostatic Hyperplasia (BPH):

One example of a condition where it is desirable to lift, compress or otherwise remove a pathologically enlarged tissue is Benign Prostatic Hyperplasia (BPH). BPH is one of the most common medical conditions that affects men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH is expected to increase as the average age of the population increases in developed countries.

The prostate gland enlarges throughout a man's life. In some men, the prostatic capsule around the prostate gland may prevent the prostate gland from enlarging further. This causes the inner region of the prostate gland to squeeze the urethra. This pressure on the urethra increases resistance to urine flow through the region of the urethra enclosed by the prostate. Thus, the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate, and the like.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine, and the like) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, Serenoa Repens (sago palm) and South African star grass are administered to the patient. Prescription medications are prescribed as first line therapy in patients with symptoms that are interfering with their daily activities. Two main classes of prescription medications are alpha-1 a-adrenergic receptors blockers and 5-alpha-reductase inhibitors. Alpha-1 a-adrenergic receptors blockers block the activity of alpha-1 a-adrenergic receptors that are responsible for causing constriction of smooth muscle cells in the prostate. Thus, blocking the activity of alpha-1 a-adrenergic receptors causes prostatic smooth muscle relaxation. This, in turn, reduces urethral resistance thereby reducing the severity of the symptoms. 5-alpha-reductase inhibitors block the conversion of testosterone to di-hydro-testosterone. Di-hydro-testosterone causes growth of epithelial cells in the prostate gland. Thus, 5-alpha-reductase inhibitors cause regression of epithelial cells in the prostate gland and, hence, reduce the volume of the prostate gland, which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus, the region of the urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases deep enough to cut the surrounding prostate gland tissue including the prostatic capsule. This releases any compression on the bladder neck and causes the bladder neck to spring apart. The incisions can be made using a resectoscope, laser beam, and the like.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium:Yttrium-aluminum-garnet (NdYAG) laser is used to ablate tissue by causing coagulation necrosis. The procedure is performed under visual guidance. In HoLEP, a holmium:Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and, hence, is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland, thus, reducing the severity of BPH symptoms.

Another example of a minimally invasive procedure for treating BPH symptoms is Transurethral Needle Ablation (TUNA). In this procedure, heat-induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser-induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra, and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360° along the terminal 3 mm of the laser fiber. The distal tip is inserted into the middle lobe of the prostate gland, and laser energy is delivered through the distal tip for a desired time. This heats the middle lobe and causes laser-induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which, in turn, causes the prostate gland to shrink. Shrinkage of the prostate gland reduces the degree of squeezing of the urethra by the prostate, thus, reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have disadvantages. Alpha-1 a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only have a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra; need for a repeat surgery; and the like. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%). Typical recovery from TURP involves several days of inpatient hospital treatment with an indwelling urethral catheter, followed by several weeks in which obstructive symptoms are relieved, but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries has made their removal quite difficult and invasive.

Thus, the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and, in fact, often experiences worse symptoms for weeks after the procedure until the body begins to heal. Additionally, all device approaches require a urethral catheter placed in the bladder, and in some cases for weeks. In some cases, catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Cosmetic or Reconstructive Tissue Lifting and Repositioning:

Many cosmetic or reconstructive surgical procedures involve lifting, compressing or repositioning of natural tissue, natural tissue or artificial grafts, or aberrant tissue. For example, surgical procedures such as face lifts, brow lifts, neck lifts, tummy tucks, and the like, have become commonplace. In many cases, these procedures are performed by creating incisions through the skin, dissecting to a plane beneath muscles and fascia, freeing the muscles, fascia and overlying skin from underlying structures (e.g., bone or other muscles), lifting or repositioning the freed muscles, fascia and overlying skin, and then attaching the repositioned tissues to underlying or nearby structures (e.g., bone, periostium, or other muscles) to hold the repositioned tissues in their new (e.g., lifted) position. In some cases, excess skin may also be removed during the procedure.

There have been attempts to develop minimally invasive devices and methods for cosmetic lifting and repositioning of tissues. For example, connector suspension lifts have been developed where one end of a standard or modified connector thread is attached to muscle and the other end is anchored to bone, periostium or another structure to lift and reposition the tissues as desired. Some of these connector suspension techniques have been performed through cannulas or needles inserted though relatively small incisions of puncture wounds.

There remains a need for the development of a suture lock or a suture anchor for use in various contemplated applications. In particular, there is a need for an anchor which can be deformed to lockingly engage suture once access to an interventional site is achieved. The disclosed embodiments address these and other needs.

SUMMARY

Briefly and in general terms, the disclosed embodiments are directed towards an anchor assembly for use within a patient's body. In one embodiment, an anchor secures to a connector in the form of a suture. The structures can further form an assembly including a distal anchor connected to a proximal anchor.

In various approaches, the anchor can include a solid generally cylindrical or alternatively a tubular back end. The anchor can also include a pair of spaced members which are configured to capture and deform the suture there between and prevent the suture from disengaging from the anchor device once engaged. Alternatively, portions of a tubular anchor body are deformable about the suture. The mechanism of suture attachment and strength of the assembly is a combination of compression of the suture between deformable structure of the anchor as well as disruption of the suture surface by the anchor. The deformable structure provides surface contact and focuses the compressive forces that cause the suture to conform about the anchor.

In one specific approach, the anchor includes legs which are deformed about a connector. In one approach, the legs assume a first open configuration and are deformed to define a closed configuration. The legs can be laterally or longitudinally deformed in various contemplated embodiments. In another approach, the anchor includes a mid-section defining a through hole and first and second ends which are twisted with respect to each other to close the hole about a connector.

In other aspects, the anchor can include a pair of spaced prongs joined together at a slot inception. Distal ends of the prongs are deformable to close the anchor about a connector. In yet another approach, the anchor can be formed by a single continuous wall defining a slot for accepting a connector. Lateral portions of the wall are deformable inwardly to securely engage the connector.

Other features and advantages will become apparent from the following detailed description, taken in conjunction with the accompanying drawings, which illustrate by way of example, the features of the various embodiments.

BRIEF DESCRIPTION OF THE DRAWINGS

FIGS. 11A-C are perspective views, depicting yet a further approach to a deformable anchor;

DETAILED DESCRIPTION

Figure 1:
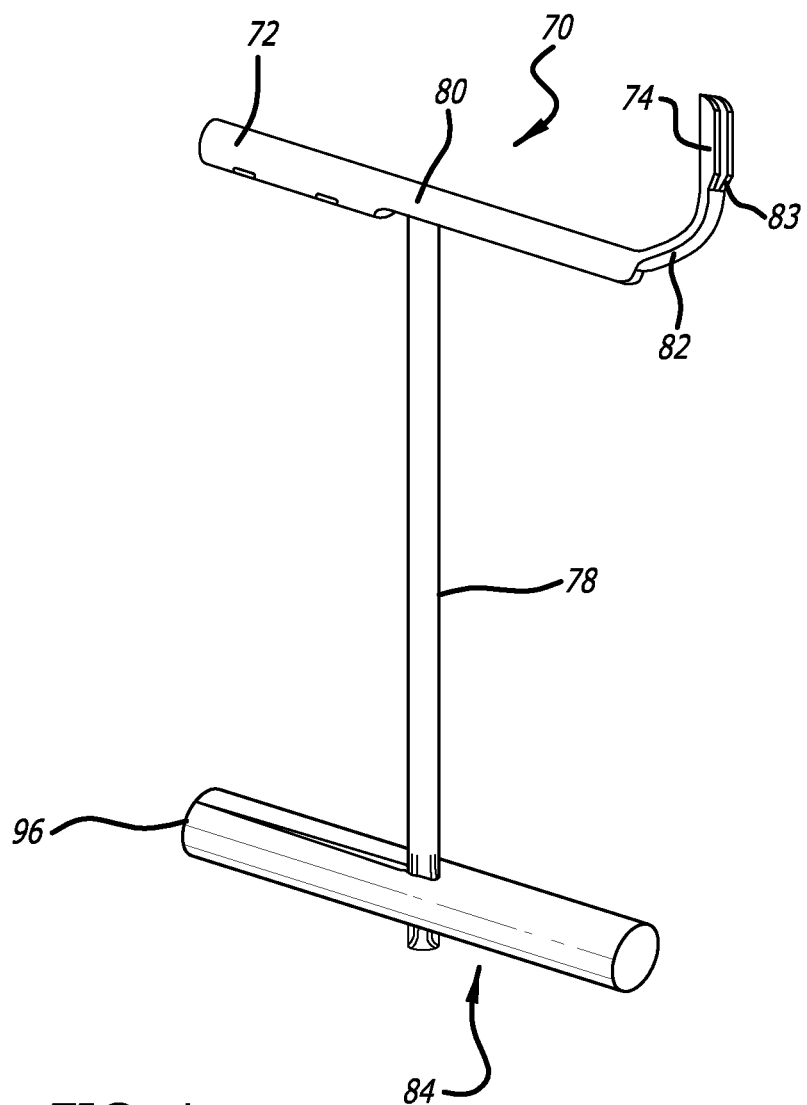
FIG. 1 is a perspective view of one embodiment of an anchor assembly that includes a distal anchor and a proximal anchor secured together by a suture.
Figure 2A:
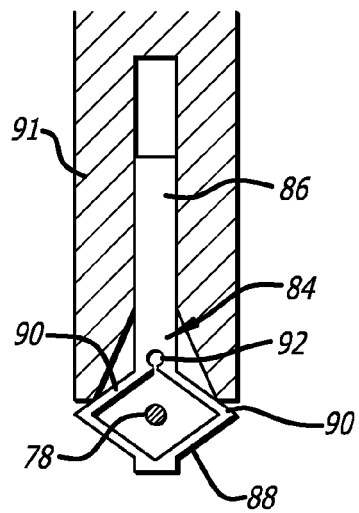
FIGS. 2A-D are side views, depicting one embodiment of a deformable anchor assembly and structure for deforming the anchor.
Figure 2B:
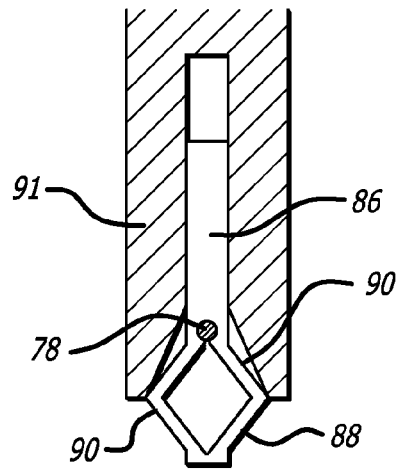
Figure 2C:
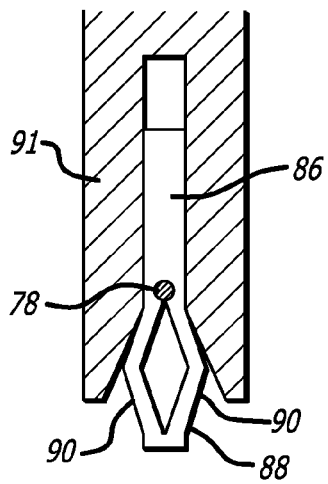
Figure 2D:
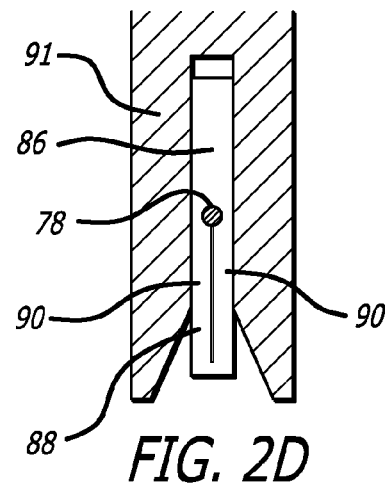

Turning now to the figures, which are provided by way of example and not limitation, the disclosed embodiments are embodied in anchor assemblies configured to be delivered within a patient's body. As stated, the disclosed embodiments can be employed for various medical purposes including but not limited to retracting, lifting, compressing, supporting or repositioning tissues, organs, anatomical structures, grafts or other material found within a patient's body. Such tissue manipulation is intended to facilitate the treatment of diseases or disorders. Moreover, the disclosed embodiments have applications in cosmetic or reconstruction purposes, or in areas relating to the development or research of medical treatments. Referring now to the drawings, wherein like reference numerals denote like or corresponding components throughout the drawings and, more particularly to FIGS. 1-15, there are shown aspects of an anchor assembly.

In such applications, one portion of an anchor assembly is positioned and implanted against a first section of anatomy. A second portion of the anchor assembly is then positioned and implanted adjacent to a second section of anatomy for the purpose of retracting, lifting, compressing, supporting or repositioning the second section of anatomy with respect to the first section of anatomy, as well as for the purpose of retracting, lifting, compressing, supporting or repositioning the first section of anatomy with respect to the second section of anatomy. It is also to be recognized that both a first and second portion of the anchor assembly can be configured to accomplish the desired retracting, lifting, compressing, supporting or repositioning of anatomy due to tension supplied thereto via a connector assembly (e.g., suture) affixed to the first and second portions of the anchor assembly.

Certain of the contemplated approaches involve proximal anchors which are placed about a connector prior to its deformation and connection to the connector which thus can eliminate a risk of the proximal anchor not catching the connector. Certain approaches also can involve slow and controlled deformation which can lead to a desirable engagement between the anchor and connector. Further, steps can be taken to strengthen the lock between anchor and connector such as by cold working the anchor material during or after deformation.

In one embodiment of the anchor assembly, the anchor assembly is configured to include structure that is capable of being implanted within a patient's body. The anchor assembly may also be used in conjunction with a conventional remote viewing device (e.g., an endoscope) so that an interventional site can be observed.

In one embodiment, the anchor assembly can be placed at an intervention site using a delivery tool. One specific, non-limiting application of the delivery tool is for the treatment of benign prostatic hyperplasia. In this procedure, an implant is delivered to a prostatic lobe that is obstructing the urethral opening and restricting flow. The implant compresses the lobe, thereby increasing the urethral opening and reducing the fluid obstruction through the prostatic urethra.

Additionally, in one embodiment, the anchor assembly is embodied in a tissue approximation anchor (TAA). The tissue approximation anchor is an implant assembly that includes one tubular member (preferably comprised of Nitinol or other comparable material), referred to as the capsular anchor or, more generally, distal anchor 70. The distal anchor 70 is preferably connected by a suture 78 to a slotted, flattened-tubular member (preferably comprised of stainless steel), referred to as the urethral anchor or proximal anchor 84. In one specific, non-limiting embodiment, the distal anchor 70 is comprised of an electro-polished Nitinol (nickel titanium alloy SE508, 55.8% nickel) tube.

The tissue approximation anchor is designed to be useable in an office environment (in contrast to requiring a hospital environment). The delivery tool is used through a 19Fr introducer sheath size in one preferred embodiment, while in another embodiment a sheath size of 21F is employed. Additionally, the material selection and construction of the tissue approximation anchor still allows for a subsequent TURP procedure to be performed, if necessary. In this suture-based, tissue approximation technique, a needle delivery mechanism is used to implant a nitinol distal anchor 70 and attached connector or suture 78. In one approach, the introducer sheath is first placed within a patient's urethra. An anchor housed within the delivery tool is then placed through the introducer sheath and a distal portion of the delivery tool is placed at the interventional site. Once the distal anchor 70 and attached suture 78 have been deployed, with the needle retracted and the suture 78 tensioned, the anchor 84 is pushed by the delivery tool and captures the suture 78 transverse to the anchor axis.

In one embodiment, the nitinol tube is attached to a USP size 0 PET (Poly Ethylene Terephthalate) monofilament suture 78 by thermally forming the suture to locking features on the distal anchor 70 (See FIG. 1). Referring again to the suture itself, the PET suture is a round monofilament extrusion/pulltrusion composed of a grade 8816 polyethylene terephthalate. Typically, the base material for the suture is annealed at approximately 191 degrees Celsius for approximately 5 minutes in a straight condition. In one non-limiting embodiment, the PET suture 78 has a diameter of 0.015 inches and a tensile strength greater than or equal to 6.0 pounds.

In one embodiment, as shown in FIGS. 2A-D, the anchor 84 includes a proximal end 86 defined by a cylinder and a distal end portion 88 that can assume both open and closed positions. The distal end 88 includes a pair of arms 90, which are bent at their mid-points and connected at distal terminal ends thereof. An anchor delivery device can include a translatable sleeve 91 which can be moved relative to the anchor 84 to deform the arms 90 so that they assume a straightened configuration. When straightened, the arms 90 grip and deform the connector 78 configured therebetween. The interior structure of the arms 90 function to disrupt the surface of the connector 78, both biting into the connector 78 as well as compressing the suture 78. The anchor 84 can further include a slot inception 92 for registering and receiving the connector 78. Deforming the arms 90 to a closed position captures the connector 78 within the slot inception 92.

Notably, in one embodiment the anchor 84 is dimensionally relative to the diameter of the suture 78 such that is has sufficient gripping force to obviate the need for a securing end unit. Accordingly, in a preferred embodiment, a second or supplemental structure is not needed.

In one embodiment, shaped tube raw stock is used to produce the anchor 84 using slot/profile cutting. Specifically, in one embodiment the raw stock may be cut by laser, wire-EDM, or stamped from a flat and formed into a shape. In one non-limiting embodiment, the raw stock has a total height ranging from 0.020 inches to 0.025 inches, and has a total width ranging from 0.038 inches to 0.042 inches. Thus, this raw stock is flatter and wider than a purely round tube would be.

The inwardly facing structure of the arms 90 of the anchor 84 is configured to grasp and deform the suture 78. It will be appreciated by those skilled in the art, that many variations such structure are possible for optimizing performance in different situations. Additionally, in some embodiments, the protrusions formed on opposite prongs may be of differing shapes. Such slot parameters include, by way of example only, and not by way of limitation: width, thickness, length, and profile. Optionally, the anchor assembly may be filled in with an RO material, or other therapeutic agent.

Figure 3A:
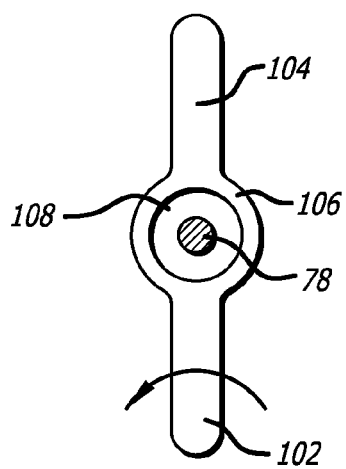
FIGS. 3A-C are side views and a perspective view, depicting another embodiment of a deformable anchor assembly and structure for deforming the anchor.
Figure 3B:
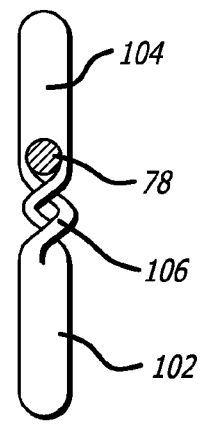
Figure 3C:
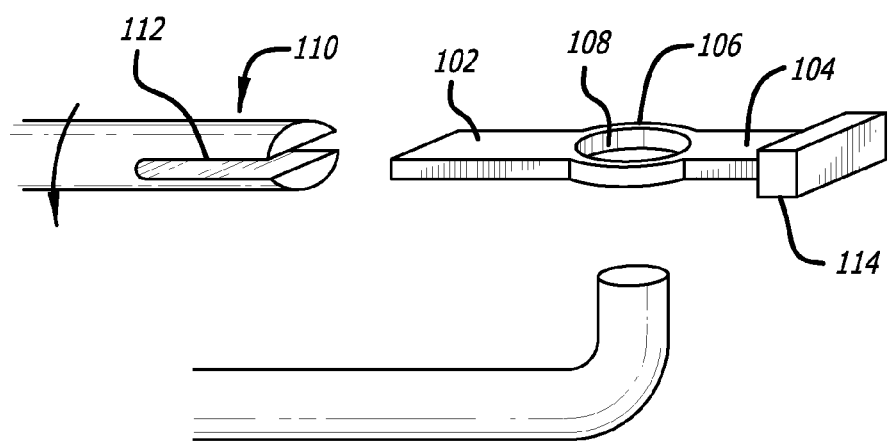
Figure 4A:
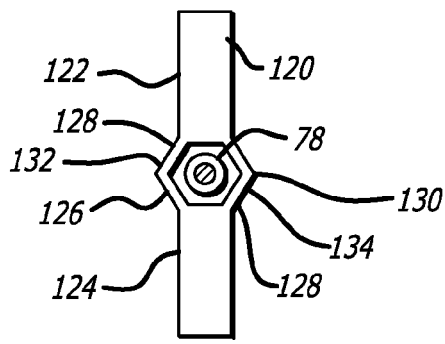
FIGS. 4A-B are side views of yet another embodiment of a deformable anchor assembly.
Figure 4B:
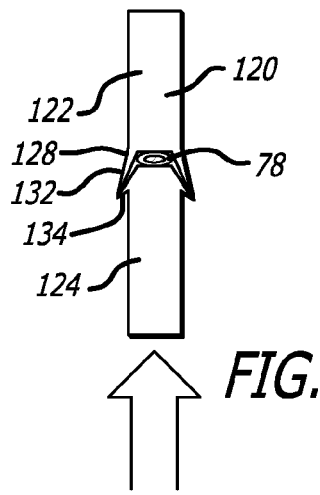

With reference to FIGS. 3A-C, in another embodiment, a proximal anchor 100 can be defined by proximal 102 and distal 104 tabs joined together at a center circular structure 106 with a hole 108 formed therethrough. The center circular structure 106 is contemplated to define deformable structure for capturing a connector. In use, a connector 78 can be threaded through the center hole 108. A delivery device can include a longitudinally rotatable arm 110 with a slot 112 formed in a distal end thereof. The slot 112 is sized and shaped to receive the proximal tab 102. The delivery device can further include a stabilizing block 114 configured to retain the distal tab 104.

To securely attach a connector 78 to the proximal anchor 100, the arm 112 is rotated so that the proximal tab 102 is in turn rotated with respect to the distal tab 104. This action results in twisting the deformable members defining the center circular structure 106 about a connector 78 threaded therethrough. In this way, the anchor 100 can be securely fixed to the connector. It should be recognized that the deformable structure of this embodiment can assume a myriad of other configurations that can be twisted about a connector.

As shown in FIGS. 4A-6, the proximal anchor 120 can also include longitudinally collapsible structure. In this embodiment, an anchor delivery apparatus (not shown) would include a driving member and a stop, between which the longitudinally collapsible anchor 120 can be deformed. Thus, the collapsible anchor 120 can include a proximal end 122 attached to a distal end 124 by a central collapsible framework 126. The collapsible framework 126 can further be defined by a pair of spaced arms 128 which initially includes bends 130. Longitudinal compression of the anchor 120 causes the arms 128 to collapse such that a first section of the arms 132 fold over a second section of the arms 134.

Figure 5:
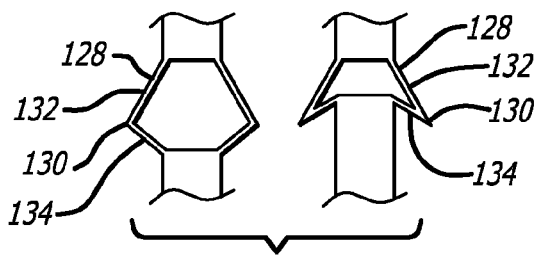
FIG. 5 is a schematic representation, depicting one alternate approach to the anchor of FIGS. 4A-B.
Figure 6:
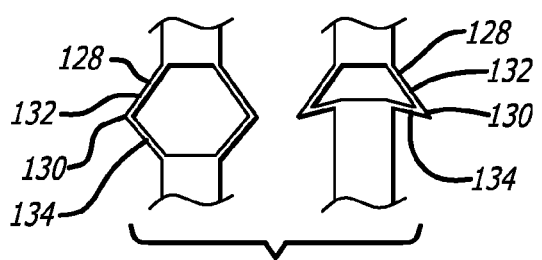
FIG. 6 is a schematic representation, depicting another approach to the anchor assembly of FIGS. 4A-B.

As best seen in FIGS. 5 and 6, the arms 128 of the collapsible anchor 120 can have various configurations. That is, in a first approach (FIG. 5), a first section 132 of the collapsible arms 128 can have a longer length than a second section 134. In other approaches, the arms 128 can have sections 132, 134 having other relative lengths. For example, as shown in FIG. 6, the sections 132, 134 can be approximately the same length. Thus, the collapsible nature of the anchor can be adjusted for a particular purpose so that a connector 78 can be best fixed to the collapsible anchor 120.

Figure 7A:
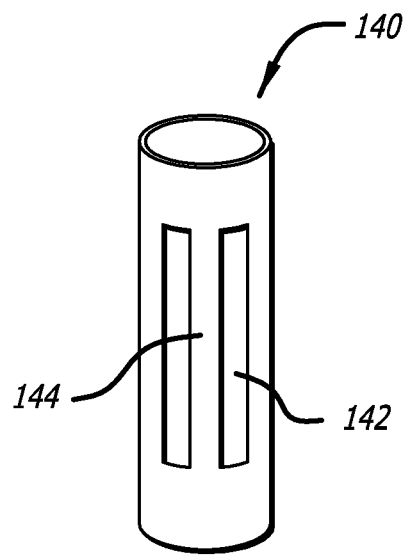
FIGS. 7A-B are perspective views, depicting a longitudinal collapsible anchor.
Figure 7B:
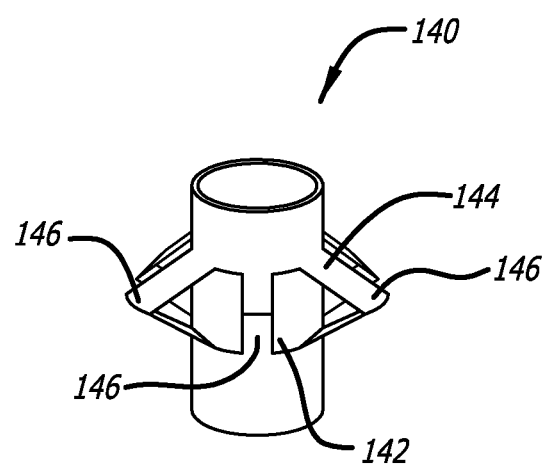
Figure 8A:
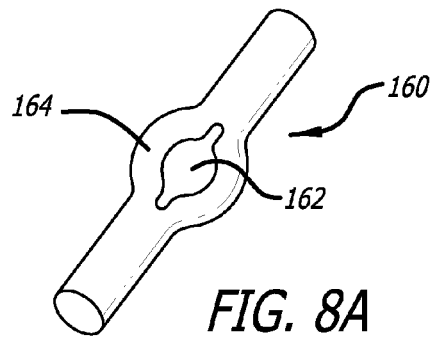
FIGS. 8A-B are perspective views, depicting a still further approach to a deformable anchor.
Figure 8B:
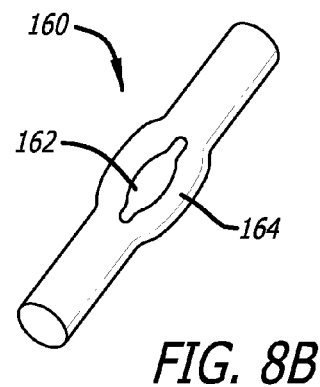
Figure 9A:
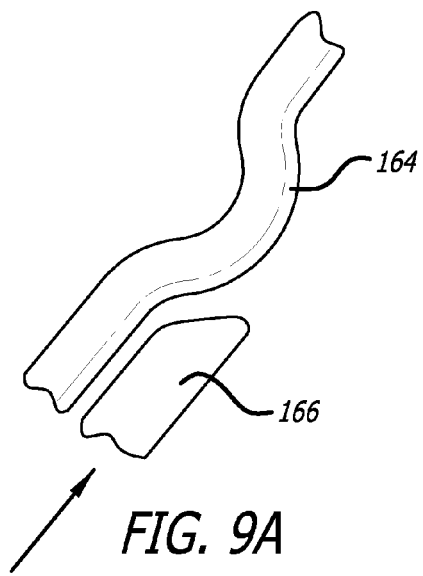
FIGS. 9A-B are schematic representations, highlighting features of the anchor of FIGS. 7A-B.
Figure 9B:
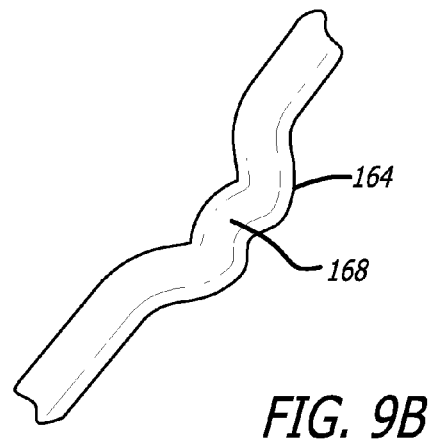
Figure 10A:
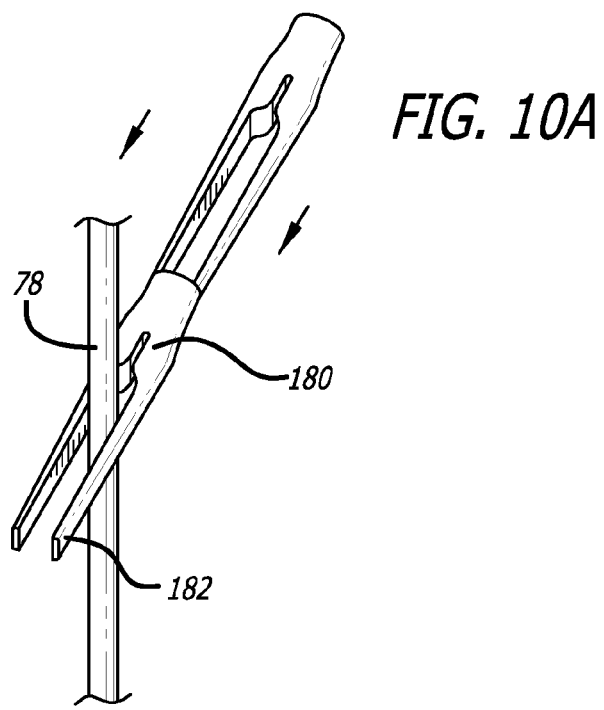
FIGS. 10A-C include a perspective view and side views, depicting a further approach to a deformable anchor.
Figure 10B:
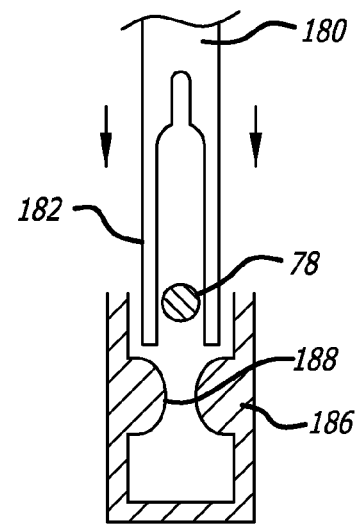
Figure 10C:
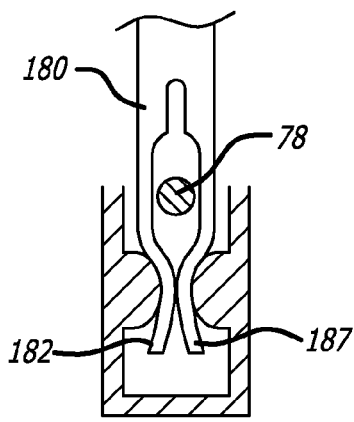
Figure 12A:
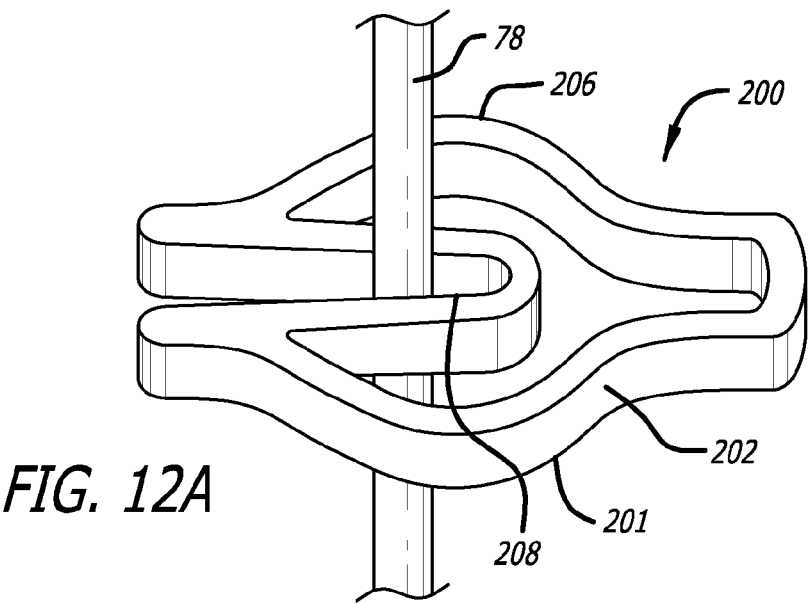
FIGS. 12A-B are still yet another deformable side view, depicting a deformable anchor with deformable walls.
Figure 12B:
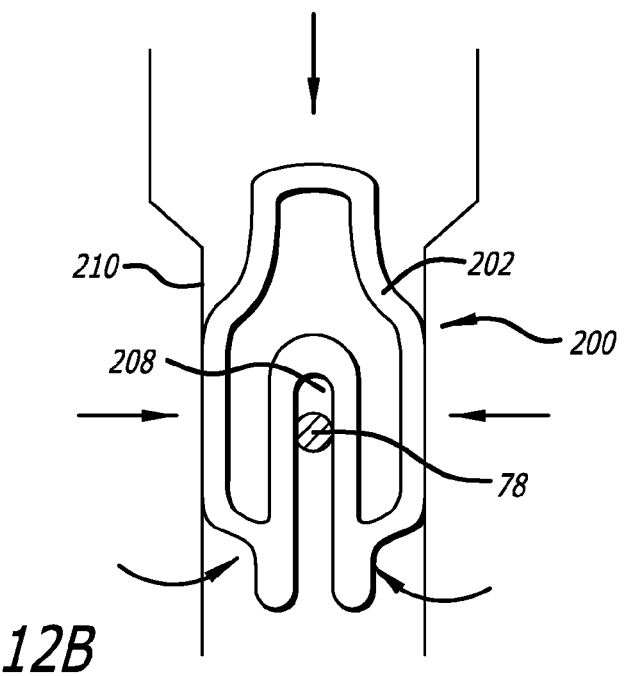

Another approach to a longitudinally collapsible anchor 140 is shown in FIGS. 7A-B. Here, a midsection of the anchor 140 includes a series of longitudinally extending slots 142. Members 144 configured between the slots 142 are designed to deform outwardly in response to forces which longitudinally collapse the anchor 140. Such projections 146 can potentially aid in fixing the anchor 140 at an interventional site.

Turning now to FIGS. 8A-B and 9A-B, additional aspects of a proximal anchor 160 are presented. In this approach, the anchor 160 is defined by a solid bar or tube with a central opening 162 that can be closed when opposing forces are placed on ends of the anchor 160. The central opening 162 can alternatively be closed about a connector (not shown) by convexly curved arms 164 defining the opening 162. Thus, it is contemplated that an anchor delivery apparatus can include an extended arm or sleeve 166 that engages the curved arms 164 to translate a portion 168 thereof against a connector to form a secure attachment. The deformed arms 164 resists opening until a force greater than expected that a connector can provide is applied to the device.

Other contemplated deformable anchors 180 can assume a pin including a pair of spaced, deformable arms 182 (See FIGS. 10A-C and 11A-C). In these embodiments, the arms 182 define a slot for receiving and securely affixing to a connector 78. The arms 182 can be deformed in various ways. In a first approach, an anchor delivery apparatus can include a sleeve 186 including a pair of internally directed projections 188 for closing and deforming the legs 182 about a connector 78. Distal terminal ends 188 of the legs 182 are permitted to flare away from each other. As shown in FIGS. 11A-C, a deforming sleeve 190 can further include forming structure 192, 194 which guides the distal terminal ends 187 of the arms to a closed position to eliminate the flares.

In yet another aspect, the deformable anchor 200 can include a single continuous wall 202 defining a perimeter of the anchor. An internal portion 204 of the anchor 200 is an open space. The wall 202 includes a pair of curved laterally extending structures 206 which present deformable structure. The wall 202 also defines a slot 208 for receiving a connector 78.

To attach the anchor 200 to a connector 78, it is contemplated that inwardly directed forces be applied to the laterally extending structures 206. In one approach, the anchor 200 can be advanced through a delivery apparatus including a narrowed section 210 which engages the lateral walls 206 and deforms them inwardly about the connector. Such action reduces the slot to thereby facilitate the walls gripping the connector.

With each of the above described embodiments, a locking engagement with a connector 78 is achieved with a deforming anchor. Again, deformation of the anchor into locking engagement can be accomplished in various conventional approaches, such as including structure that transmits a force in lateral and longitudinal directions.

Figure 13:
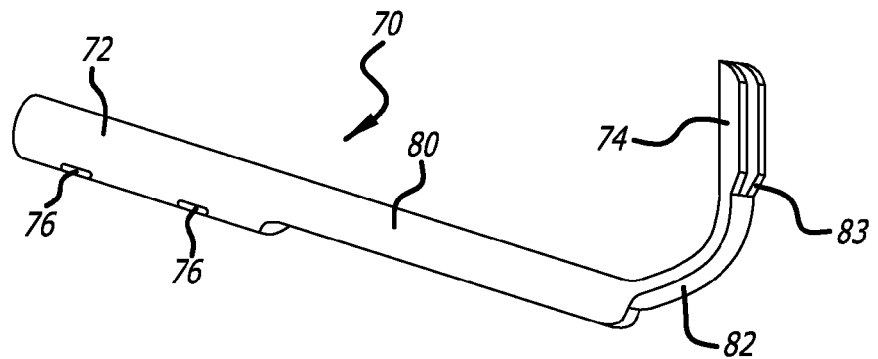
FIG. 13 is a side view of a deformable anchor with a orthogonally oriented tail portion.
Figure 14:
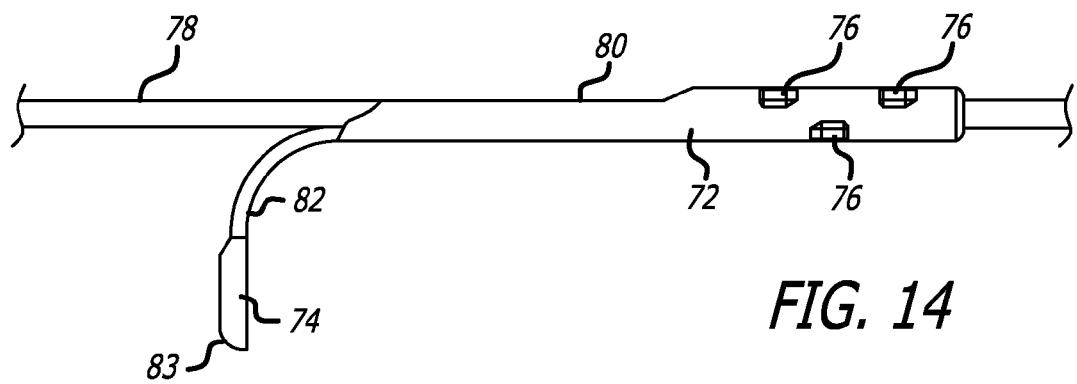
FIG. 14 is a side view of the distal anchor with a orthogonally oriented tail portion of FIG. 14 attached to a connector.

One embodiment of a distal anchor assembly 70 is depicted in FIGS. 13 and 14. In its unconstrained configuration, the distal (e.g., capsular) anchor 70 includes a tubular (head) portion 72 which is generally orthogonally oriented to a tail portion 74. It is to be noted, however, that while housed in a delivery assembly and prior to deployment at a target area, the distal anchor 70 is constrained to define a generally straight configuration, only subsequently assuming the unconstrained (i.e., orthogonally oriented) configuration upon deployment from a delivery device.

The distal anchor 70 is laser cut or wire EDM (electrical discharge machined) from a nitinol base stock that is generally-tubular is shape. The Nitinol distal anchor is shape-set to have a "flipping tail" and is electro-polished. The connector 78 is then attached to the distal anchor 70 as an adhesive free joint. Specifically, in one embodiment, the PET suture 78 is thermoformed onto locking features in the anchor 70. The distal anchor 70 may be locally heated to re-flow the suture onto the end of the anchor 70 and into cutouts on the anchor 70. Continuing, in one non-limiting embodiment, the post electro-polished distal anchor 70 has a 0.016 inner diameter and a 0.0253 outer diameter.

In one non-limiting embodiment, the tubular portion 72 of the distal anchor 70 includes a plurality of tabs 76 which can be deformed or deflected to accomplish affixing the distal anchor 70 to a suture 78. It has been found that three such tabs 76, two on one side of the tubular portion 72 and one on an opposite side, provide a sufficient connecting force and a desired balance between the suture 78 and distal anchor 70 and to move the distal anchor 70 by applying a force either in the proximal or distal direction. However, the distal anchor 70 may be attached to the suture 78 through any of several known techniques, such as by being attached to the distal end of the tubular portion 72.

In another aspect of a non-limiting embodiment, t is contemplated that the distal anchor 70 can be laser cut from a tube formed of Nitinol or other appropriate material. A mid-section 80 of the distal anchor 70 provides a structural transition from the tubular portion 72 to the tail portion 74. As such, a portion of a side wall is removed in the mid-section area 80. A further portion of the side wall is removed to define a connector section 82 of the tail 74 which extends from the mid-section 80. In one embodiment, this connector section 82 includes a bend that creates the orthogonally oriented configuration. This connector section 82 acts as a barb or deflected strut to cause flipping (creating a "flipping tail") and produce the relative unconstrained (orthogonally oriented) angle assumed between the tail 74 and tubular portion 72 of the distal anchor 70. The recovered shape of the terminal end portion 83 of the anchor presents a transverse strut that engages tissue when the suture is tensioned.

Thus, in its pre-implanted form, the anchor assembly can include a distal anchor 70 (e.g., first anchor) whose initial engagement with a suture 78 is generally coaxial, and a proximal anchor 84 (e.g., second anchor) with an initial engagement being generally perpendicular with the suture 78.

As stated above, an introducer sheath (not shown) can first be placed within a patient's urethra for the purpose of facilitating access to a treatment site. The distal anchor 70 is "unsheathed" from the needle delivery mechanism once positioned for reliable deployment eliminating predicate distal suture. This results in an adjustable implant length. This distal anchor 70 configuration also provides increased yield and strength.

With reference now to FIGS. 15A-F, in one particular, non-limiting use in treating a prostate, an elongate tissue access portion 404 of a delivery device 400 is placed within a urethra (UT) leading to a urinary bladder (UB) of a patient. The delivery device can be placed within an introducer sheath previously positioned in the urethra or alternatively, the delivery device can be inserted directly within the urethra. The patient is positioned in lithotomy. The elongate portion 404 is advanced within the patient until a leading end 410 thereof reaches a prostate gland (PG). In a specific approach, the side(s) (i.e., lobe(s)) of the prostate to be treated is chosen while the device extends through the bladder and the device is turned accordingly. The device is first positioned at the bladder neck and then retracted approximately 1 cm while keeping the device parallel to the prostatic fossa and preserving mucosa. The distal end of the elongate portion can be used to push the urethra into the prostate gland. The inside of the prostate gland (i.e., adenoma) is spongy and compressible and the outer surface (i.e., capsule) of the prostate gland is firm. By the physician viewing with the endoscope, he/she can push the urethra into the prostate gland compressing the adenoma and creating the desired opening through the urethra. To accomplish this, the physician pivots the tool laterally about the pubic symphysis, generally about 20 to 30 degrees (See FIG. 15A). The physician then rotates the tool anterior between 9 and 10 o'clock for the patient's side right lobe and between 2 and 3 o'clock for the patient's side left lobe. Viewing through the endoscope, the physician wants to have about the same amount of tissue protruding on both sides of the elongate shaft (See FIG. 15B).

Figure 15A:
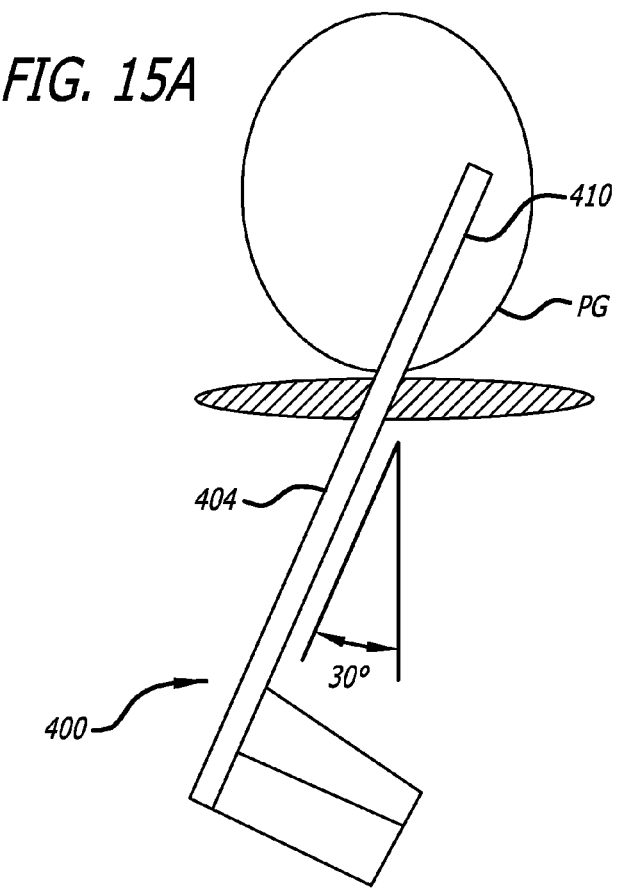
FIGS. 15A-F are partial cross sectional views of an anchor assembly of FIG. 1 being implanted through the prostate of an individual with Benign Prostatic Hyperplasia.
Figure 15B:
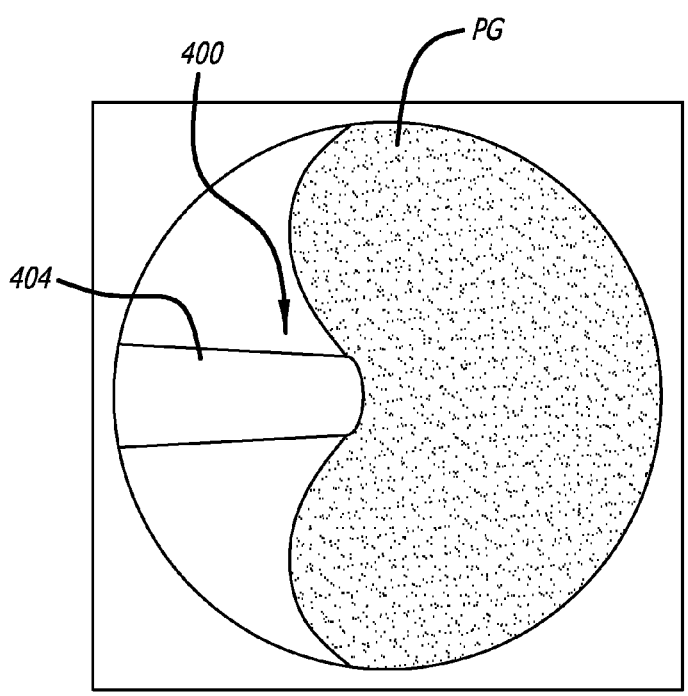
Figure 15C:
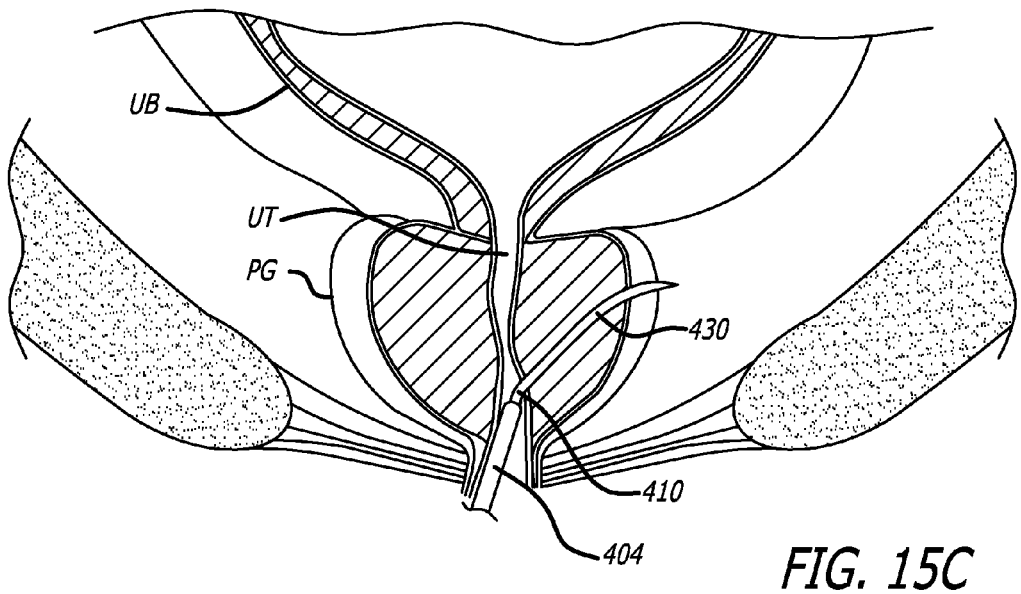
Figure 15D:
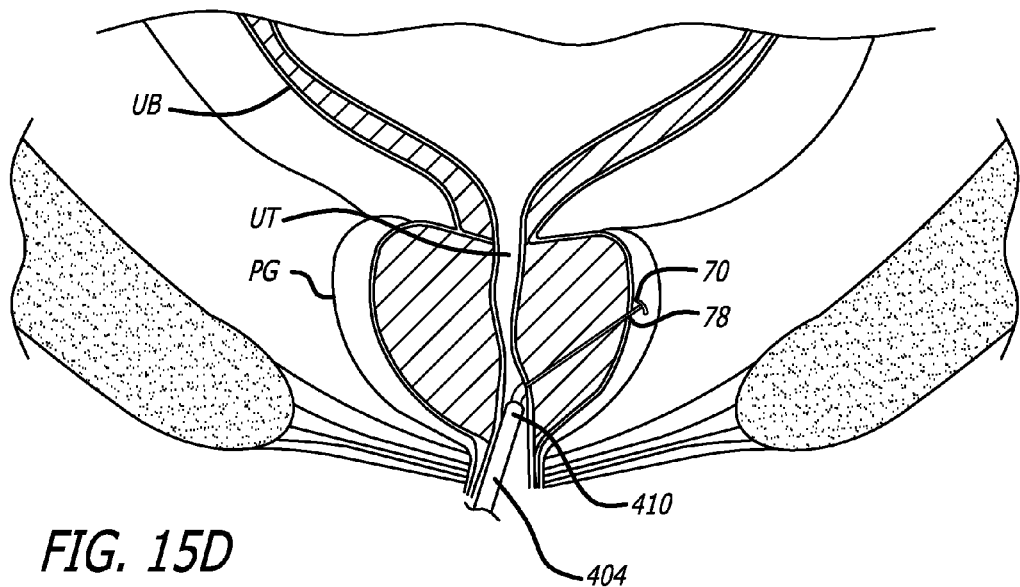

At the leading end 410 of the delivery device, as shown in FIG. 15C, a needle 430 carrying an anchor assembly is ejected into and through tissue. The needle assembly can be configured so that it curves back toward the delivery tool as it is ejected. In use in a prostate intervention, the needle assembly 430 is advanced through and beyond a prostate gland (PG). The delivery device can be rotated anteriorly to lift a prostatic lobe.

Figure 15E:
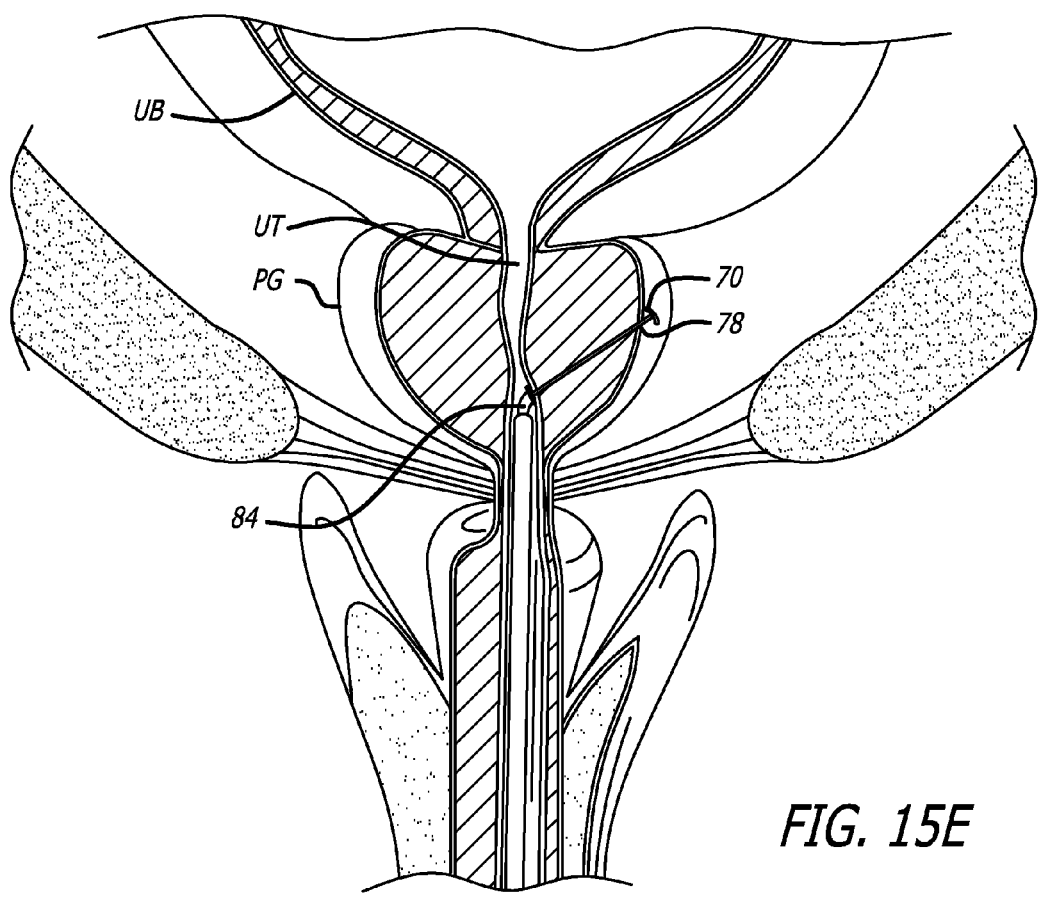

Upon withdrawal of the needle assembly 430 (See FIG. 15D), the distal anchor 20 is left beyond the prostate (PG). Next, steps are taken to implant the proximal anchor 84 within the urethra (FIG. 15E). Either a single anchor assembly or multiple anchor assemblies can be delivered and deployed at an intervention site by the deployment device (See FIG. 15F). Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the compression of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

The disclosed embodiments contemplate both pushing directly on anchor portions of an anchor assembly as well as pushing directly upon the connector of the anchor assembly. Further, an anchor assembly can be delivered and deployed at an interventional site by a deployment device. Consequently, in the context of prostate treatment, the disclosed embodiments accomplish both compressing of the prostate gland and the opening of the prostatic urethra and applying tension between ends of the implant. Moreover, drug delivery is contemplated as a further remedy in BPH and over-active bladder treatment.

Once implanted, the anchor assembly of the disclosed embodiments accomplishes desired tissue approximation, manipulation, compression or retraction, as well as cooperates with the target anatomy to provide an atraumatic support structure. In particular, the shape and contour of the anchor assembly can be configured so that the assembly invaginates within target tissue, such as within natural folds formed in the urethra by the opening of the urethra lumen by the anchor assembly. In fact, in situations where the anchor assembly is properly placed, wispy or pillowy tissue in the area collapses around the anchor structure. Eventually, the natural tissue can grow over the anchor assembly, and new cell growth occurs over time. Such cooperation with target tissue facilitates healing and avoids unwanted side effects such as calcification or infection at the interventional site.

Furthermore, in addition to an intention to cooperate with natural tissue anatomy, the disclosed embodiments also contemplate approaches to accelerate healing or induce scarring. Manners in which healing can be promoted can include employing abrasive materials, textured connectors, biologics and drugs.

Figure 15F:
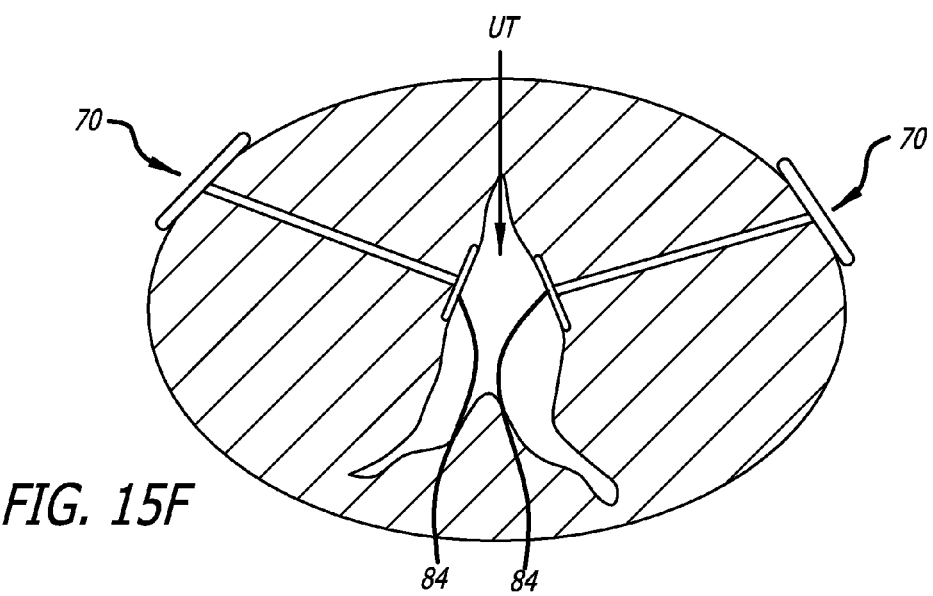

It has been observed that placing the anchors at various desired positions within the anatomy can extract the best results. For example, when treating a prostate, one portion of an anchor can be placed within a urethra. It has been found that configuring such anchors so that ten o'clock and two o'clock positions (when looking along the axis of the urethra) are supported or retained, effectively holds the anatomy open and also can facilitate invagination of the anchor portion within natural tissue. Typically, one to two pairs of anchor assemblies are implanted to create an anterior channel along the urethra within the prostate gland (FIG. 15F). This is particularly true in the regions of anatomy near the bladder and the juncture at which the ejaculatory duct connects to the urethra.

Moreover, it is to be recognized that the foregoing procedure is reversible. In one approach, the connection of an anchor assembly can be severed and a proximal (or second) anchor component removed from the patient's body. For example, the physician can simply cut the connector and simultaneously remove the second anchor previously implanted for example, in the patient's urethra. It is to be recognized that various materials are contemplated for manufacturing the disclosed devices. Moreover, one or more components such as distal anchor 70, proximal anchor 84, suture 78, of the one or more anchor assemblies disclosed herein may be designed to be completely or partially biodegradable or bio-fragmentable.

Further, as stated, the systems and methods disclosed herein may be used to treat a variety of pathologies in a variety of tubular structures comprising a cavity or a wall. Examples of such organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, and the like.

Finally, it is to be appreciated that the invention has been described hereabove with reference to certain examples or embodiments, but that various additions, deletions, alterations and modifications may be made to those examples and embodiments without departing from the intended spirit and scope of the disclosed embodiments. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

The various embodiments described above are provided by way of illustration only and should not be construed to limit the disclosed embodiments. Those skilled in the art will readily recognize various modifications and changes that may be made to the disclosed embodiments without following the example embodiments and applications illustrated and described herein, and without departing from the true spirit and scope of the disclosed embodiments, which is set forth in the following claims.

What is claimed:

1. An anchor assembly for use in treating body tissue, comprising:
    a distal anchor;
    a connector; and
    a proximal anchor, the proximal anchor including a deformable portion and a non-deformable portion spaced longitudinally from the deformable portion, the deformable portion including a first space defined by a first configuration of spaced legs with connected terminal ends at each end of the legs and sized to receive the connector; wherein legs are configured to collapse inwardly about the non-deformable portion in part or completely to a second space defined by a second configuration of spaced legs, the second configuration having a lateral width less than the lateral width of the first configuration and wherein the legs are configured to capture and deform the connector therebetween.

2. The anchor assembly of claim 1, wherein the legs can assume an open position and a closed position.

3. The anchor assembly of claim 2, wherein the legs include a bend positioned at a mid-section of the legs.

4. The anchor assembly of claim 1, wherein the anchor further including a slot inception.

5. The anchor assembly of claim 1, distal anchor comprising a laterally oriented tail.

6. The anchor assembly of claim 5, the distal anchor further comprising a tubular portion which is generally perpendicular to a tail portion.

7. The anchor assembly of claim 6, wherein the tubular portion includes tabs for affixing the distal anchor to the connector.

8. An anchor assembly, comprising:
a distal anchor;
a connector; and
a proximal anchor, the proximal anchor including a deformable portion, the deformable portion being defined by longitudinally collapsible structure, and a non-deformable portion spaced longitudinally from the deformable portion, the deformable portion including a closed space having a first lateral width defined by spaced legs sized to receive the connector; wherein legs are configured to include a bend prior to collapse and to collapse about the non-deformable portion to define a closed space having a second lateral width less than the first lateral width to capture and deform the connector therebetween.

9. The anchor assembly of claim 8, wherein the bend is at a midpoint of the legs.

10. The anchor assembly of claim 8, further comprising a first non-deformable portion and a second non-deformable portion, wherein the deformable portion is configured between the first and second non-deformable portions.

11. The anchor assembly of claim 10, wherein the legs include a bend positioned closer to the first non-deformable portion than the second non-deformable portion.

12. An anchor assembly, comprising:
a distal anchor;
a connector; and
a proximal anchor having a longitudinal dimension, the proximal anchor including a deformable portion, the deformable portion being defined by longitudinally collapsible structure, and a non-deformable portion spaced longitudinally from the deformable portion, the deformable portion including a space defined by spaced legs sized to receive the connector; wherein a mid-section of the legs is configured to bend inward about the non-deformable portion with respect to the longitudinal dimension to capture and deform the connector therebetween.

13. The anchor assembly of claim 12, the deformable portion further including a plurality of slots defined by radially spaced longitudinal members.

14. The anchor assembly of claim 13, wherein the radially spaced members project laterally outward when the assembly is deformed longitudinally.

15. An anchor assembly for use in treating body tissue, comprising:
a distal anchor;
a connector; and
proximal anchor means for attaching to the connector, the proximal anchor means including a deformable portion and a non-deformable portion spaced longitudinally from the deformable portion, the deformable portion including a closed space defined by spaced legs with connected terminal ends and sized to receive the connector, wherein legs initially including a bend are configured to collapse inwardly about the non-deformable portion to define straightened members to capture and deform the connector therebetween.

16. An anchor assembly, comprising:
a distal anchor;
a connector; and
proximal anchor means for attaching to the connector and having a longitudinal dimension, the proximal anchor including a deformable portion, the deformable portion being defined by longitudinally collapsible structure, and a non-deformable portion spaced longitudinally from the deformable portion, the deformable portion including a closed space defined by initially bent and spaced legs sized to receive the connector, wherein legs are configured to bend inwardly about the non-deformable portion and generally perpendicular to the longitudinal dimension to capture and deform the connector therebetween.

* * * * *